(12) United States Patent
Metzger

(10) Patent No.: US 10,625,042 B2
(45) Date of Patent: Apr. 21, 2020

(54) TREATMENT OF CENTRAL NERVOUS SYSTEM CONDITIONS USING SENSORY STIMULUS

(71) Applicant: Phoenix NeuroStim Therapeutics, LLC, Providence, RI (US)

(72) Inventor: Steven Metzger, Providence, RI (US)

(73) Assignee: Phoenix NeuroStim Therapeutics, LLC, Providence, RI (US)

( * ) Notice: Subject to any disclaimer, the term of this patent is extended or adjusted under 35 U.S.C. 154(b) by 364 days.

(21) Appl. No.: 15/034,328

(22) PCT Filed: Nov. 4, 2014

(86) PCT No.: PCT/US2014/063827
§ 371 (c)(1),
(2) Date: May 4, 2016

(87) PCT Pub. No.: WO2015/066679
PCT Pub. Date: May 7, 2015

(65) Prior Publication Data
US 2016/0279380 A1 Sep. 29, 2016

Related U.S. Application Data

(60) Provisional application No. 61/899,471, filed on Nov. 4, 2013.

(51) Int. Cl.
*A61M 21/00* (2006.01)
*A61N 1/36* (2006.01)

(52) U.S. Cl.
CPC ......... *A61M 21/00* (2013.01); *A61N 1/36014* (2013.01); *A61N 1/36025* (2013.01);
(Continued)

(58) Field of Classification Search
CPC .............. A61N 1/36025; A61N 1/0534; A61N 1/36017; A61N 1/0529; A61B 5/0482;
(Continued)

(56) References Cited

U.S. PATENT DOCUMENTS 8,190,263 B2 5/2012 Machado et al.
8,380,316 B2 2/2013 Hagedorn et al.
(Continued)

FOREIGN PATENT DOCUMENTS

DE 10 2012 002 436 A2 8/2013
EP 2801389 A1 11/2014
(Continued)

OTHER PUBLICATIONS

Extended European Search Report for European Application No. EP 14859074.8 dated Jul. 24, 2017.
(Continued)

*Primary Examiner* — Christine H Matthews
(74) *Attorney, Agent, or Firm* — Wolf, Greenfield & Sacks, P.C.

(57) ABSTRACT

The invention discloses methods and systems for modulation of the central nervous system and more particularly for modulation of brain oscillatory activity and the brain networks that give rise to it. The methods involve using one or more non-invasive stimuli, either alone or in combination, to increase, decrease, or otherwise modulate neural oscillations, the rhythmic and/or repetitive electrical activity generated spontaneously and in response to stimuli by neural tissue in the central nervous system. Various embodiments concern methods and devices for detecting sub-optimal or pathological neural oscillatory patterns, developing treatment protocols to modify the neural oscillations in a desired manner, introducing a non-invasive stimulus or stimuli through one or more sensory pathways to treat the condi-
(Continued)

tions, and for adjusting the treatment protocol to optimize the therapeutic effect of the stimulus or stimuli.

17 Claims, 3 Drawing Sheets

(52) U.S. Cl.
CPC ............... *A61M 2021/0022* (2013.01); *A61M 2021/0027* (2013.01); *A61M 2021/0044* (2013.01)

(58) Field of Classification Search
CPC . A61B 5/40; A61B 5/4094; A61M 2021/0027
See application file for complete search history.

(56) References Cited

U.S. PATENT DOCUMENTS

| 8,494,627 | B2 | 7/2013 | Bikson et al. | |
|---|---|---|---|---|
| 2004/0116978 | A1* | 6/2004 | Bradley | A61N 1/08 607/48 |
| 2004/0173220 | A1* | 9/2004 | Harry | A43B 3/0005 128/892 |
| 2007/0043268 | A1 | 2/2007 | Russell | |
| 2007/0043401 | A1 | 2/2007 | John | |
| 2007/0142874 | A1 | 6/2007 | John | |
| 2008/0177352 | A1 | 7/2008 | Pascual-Leone et al. | |
| 2010/0048985 | A1 | 2/2010 | Henke et al. | |
| 2011/0029044 | A1 | 2/2011 | Hyde et al. | |
| 2012/0310298 | A1 | 12/2012 | Besio et al. | |
| 2013/0066137 | A1 | 3/2013 | Hulvershorn | |

FOREIGN PATENT DOCUMENTS

| WO | WO 2007/138598 A2 | 12/2007 |
|---|---|---|
| WO | WO 2013/192582 A1 | 12/2013 |

OTHER PUBLICATIONS

International Search Report and Written Opinion for International Application No. PCT/US2016/030707 dated Jul. 6, 2016.
International Search Report and Written Opinion for International Application No. PCT/US2014/63827 dated Feb. 13, 2015.
International Preliminary Report on Patentability for International Application No. PCT/US2014/63827 dated May 19, 2016.

* cited by examiner

TREATMENT OF CENTRAL NERVOUS SYSTEM CONDITIONS USING SENSORY STIMULUS

CROSS-REFERENCE TO RELATED APPLICATIONS

This Application is a national stage filing under 37 U.S.C. § 371 of International Application No. PCT/US2014/063827, filed Nov. 4, 2014, entitled "TREATMENT OF CENTRAL NERVOUS SYSTEM CONDITIONS USING SENSORY STIMULUS," which claims priority under 35 U.S.C. § 119(e) to U.S. Provisional Application Ser. No. 61/899,471 filed Nov. 4, 2013, each of which is incorporated by reference in its entirety.

BACKGROUND OF THE INVENTION

The present invention relates to modulation of the central nervous system by introducing a stimulus or stimuli to one or more sensory pathways and, more particularly, to modulation of neural oscillatory patterns associated with a neurological condition.

The brain is estimated to contain over 100 billion neurons and almost 1 trillion connecting synapses. To harness the amazing processing capabilities that this population gives rise to, the brain relies on communication both within and between a large and diverse group of specialized structures. These cortio-cortical regions are connected through the mechanism of synchronized neural oscillation—the rhythmic and/or repetitive electrical activity generated spontaneously and in response to stimuli by neural tissue. Functionally, neural oscillations are a prominent feature of brain activity. And, the synchronization of these oscillations, which reflects the temporally precise interaction of neural assemblies, is the putative mechanism whereby brain regions sub-serving specific functions communicate with each other in order to accomplish perception, cognition, and action.

By convention, neural oscillations, more commonly known as brainwaves, are divided into five frequency bands, each of which is believed to play a variety of distinct roles in normal brain function and, of importance to the present invention, can also be the underlying cause of neurological dysfunction.

Table of Brainwave Frequencies

| Frequency Range | Symbol and Name |
| --- | --- |
| f < 4 Hz | δ (delta frequency band) |
| 4 Hz-8 Hz | Φ (theta frequency band |
| 8 Hz-13 Hz | α (alpha frequency band) |
| 13 Hz-35 Hz | 13 (beta frequency band) |
| 35 Hz-200 Hz | γ (gamma frequency band) |

The role of brainwaves as the essential building blocks in sensory-cognitive processes has become a central tenet of modern neuroscience. Even simple sensory, motor and cognitive tasks depend on the precise coordination of many brain areas. And, as no behaviorally relevant task is performed independently by a single neuron, communication is of the utmost importance. Thus, ultimately, optimal brain performance relies on optimal communication.

The brain's dependency on neural oscillation and synchrony has led to the belief that the vast majority of neurological conditions are caused by defects in the brain's ability to communicate internally. Numerous clinical studies have shown that event-related oscillations in the alpha, beta, gamma, delta, and theta frequency windows are highly modified throughout the cortex in pathologic brains, particularly so in patients with cognitive impairments such as schizophrenia, autism, epilepsy and attention deficit disorder. Moreover, evidence is emerging that patterns of synchronization and de-synchronization are fundamental to the proper functioning of neural assemblies. For example, an abnormal pattern of synchronization/de-synchronization in parts of the motor system is believed to be a key pathophysiological mechanism underlying the motor symptoms, such as tremor and poverty of movement, in Parkinson's disease.

Commonly, patients with these and similar conditions are initially treated with drugs. While a large proportion of these patients may be aided by pharmaceutical interventions, many are not helped by medication, or are not helped sufficiently to provide the desired levels of relief. In these cases, more aggressive interventions, such as Deep Brain Stimulation (DBS) are often recommended.

Deep brain stimulation suffers from many disadvantages, the most obvious being the significant risks associated with open cranial surgery and the risk of damage to areas of the brain adjacent to the insertion route of the stimulation electrodes. Further, it has been shown that the electrical stimulus employed by DBS devices can damage surrounding tissue and even distal areas of the brain connected to the site of stimulation.

More recently, a number of less invasive neurostimulation technologies have become available. These technologies, most notably transcranial magnetic stimulation and transcranial electric stimulation have shown some efficacy in treating tinnitus, migraines, depression and epilepsy. However, the observed therapeutic effects of these treatments have generally not persisted for significant periods of time beyond the treatment window. And, because of safety concerns and other reasons these modalities cannot be administered outside a clinical setting, the long-term benefit of these technologies remains in question.

Therefore, there is a need to treat the foregoing example medical conditions and other neurological disorders resulting from defective neural synchrony without the use of pharmaceuticals, implanted neurostimulation devices or transcranial neuromodulation technologies.

SUMMARY OF THE INVENTION

It is known the presence of certain kinds of "noise" can enhance the detection and transmission of weak signals in nonlinear systems, such as the human nervous system, via a mechanism known as stochastic resonance (SR). The phenomenon of SR, which is counterintuitive given that noise is generally considered to interfere with perception, is based on the concept that the addition of low-level noise lowers the threshold of the system so that small signals or stimuli, which in a no-noise environment would not be discernible, are now apparent. The simplest examples of an SR-related benefit can be seen in the detection of sensory signals. For instance, SR has been found in audition, vision, and touch where stochastic noise improves sensory discriminability. Therefore, it is an aspect of the present invention to modulate the performance of the somatosensory, auditory, and visual sensory systems through the introduction of one or more stochastic stimuli.

Moreover, there is recent empirical evidence suggesting that central information processing and cognitive performance are also facilitated by the addition of optimal amounts of random noise. For example, it has been demonstrated that the addition of auditory noise improved the speed of arithmetic computations and recall on visual memory tasks in ADHD children. It is believed that SR has several different beneficial modes of action in the brain. Recent studies have convincingly shown that in neural assemblies, noise can induce new, more ordered, regimes, lead to the formation of more regular structures or increase the degree of coherence and cause the amplification of weak signals. Other studies have shown SR as both enhancing the local neural synchronization responsible for initial stimulus processing and indexed by local changes in spectral power in various frequency bands, as well as enhancing stochastic phase locking between distant brain regions cooperating in a network to manage processing of the effects of external stimuli. These results imply that SR-mediated neural synchronization is a general mechanism of brain functioning. In other words, noise can play a multifaceted role in enhancing the performance of the nervous system. Thus, in one aspect, provided is a method of promoting beneficial neural oscillation through the addition of optimal amounts of external noise to the central nervous system and thereby improving cognitive performance.

SR is usually quantified by plotting its effect on information transfer as a function of noise intensity. This relationship follows an inverted U-curve function, where performance peaks at a moderate noise level. That is, there is an optimal level of noise is maximally beneficial for performance; whereas a less than optimal amount has a diminished effect and a larger than optimal amount attenuates performance. Therefore, through the mechanism of SR, it is possible to both promote neural synchrony by the addition of beneficial amounts of noise, and by adding excessive amounts of noise, inhibit or destroy neural synchrony. Thus, in another aspect, provided is a method of introducing greater than optimal amounts of external noise to the central nervous system for the purposes of de-synchronizing pathological neural oscillation and thereby improving cognitive performance.

Projections from the auditory, visual and somatosensory cortexes reach throughout the brain, reflecting their importance to the performance of cognitive and motor functions. It is well known that sensory stimuli have a profound effect on the excitation of diverse regions within the brain. Support for the ability of the sensory pathways to affect cognitive function, and more specifically brainwave function, can be found in numerous neuroimaging studies. Moreover, it has also been shown that the auditory, visual and somatosensory pathways preferentially stimulate different cortical regions and give rise to synchronized neural oscillations between the stimulated cortexes and to other structures within the brain. Therefore, it is another aspect of the current invention to utilize the differential effect that the sensory pathway through which a stimulus is presented has on the evoked response to the stimulus within the brain to modulate neural oscillation within the central nervous system for the purpose of improving cognitive function.

In addition to being highly integrated with brain structures, there is clinical evidence that the somatosensory, auditory and visual pathways are also tightly integrated with each other and that a stimulus presented to one sense can influence the performance or functioning of the others. For example, as demonstrated by Faubert in U.S. Pat. No. 8,369,995 certain auditory stimuli can increase tactile sensitivity on a fingertip. And in a paper entitled "Oscillatory frontal theta responses are increased upon bisensory stimulation" (Clinical Neurophysiology 111, (2000) 884-893) Sakowitz et al found that amplitude of theta responses showed a considerable increase dependent on simultaneous stimulus presentation, whereas the amplitude of alpha responses appeared to be only moderately enhanced or even depressed. Further, the study results demonstrated that depending on whether the stimulus presentation was auditory, visual or bimodal, it was possible to vary the location and intensity of the evoked pattern of alpha and theta brainwaves. Therefore, depending on the choice of sensory pathway and whether a stimulus presentation is uni- or bi-modal, it is possible to modulate the brain's response to a specific stimulus. It is another aspect of the current invention to utilize the differential effect of whether a stimulus presentation is uni- or multi-modal, has on the evoked response to the stimulus within the brain to modulate neural oscillation within the central nervous system for the purpose of improving cognitive function.

The sensory pathways are also able to deliver frequency-specific stimuli to targeted brain structures. Which is to say that a 40 Hz stimulus presented through the auditory or visual sensory pathways will preferentially promote the creation of brain waves with frequencies centered around 40 Hz. Therefore, by choosing a stimulus frequency that corresponds to the brainwave frequency band of interest (i.e. alpha, beta, theta, delta and gamma) it is possible to differentially stimulate or inhibit neural synchrony in that frequency band. Also, it is known that the cortical regions of the brain preferentially use specific frequency bands to accomplish specific tasks. For example, brainwaves in the gamma band account for the majority of neural activity in the cortical—hippocampal network and are believed to be largely responsible for higher cognitive function and episodic memory. Therefore, it is a further aspect of this invention use stimuli that are bandwidth limited to preferentially modulate neural oscillation within neural signaling networks connecting specific regions of the central nervous system for the purpose of improving cognitive function.

Neuroimaging data has shown that there are often multiple brain structures and/or brain networks underlying many neurological disorders. Therefore, therapeutic interventions designed to bring about a desired change in a target area of the brain may lead to changes in other areas and these other changes can be responsible for reduced efficacy of the treatment and unwanted side effects. It is therefore an aspect of the invention to recognize, address, and utilize the interactions that exist between different brain regions of a brain network and the neural signaling pathways that connect them to provide improved treatment for neurological disorders.

It is an object of the invention to provide methods and systems for neuromodulation, control, and responsive neuromodulation which provide for observing, evaluating and utilizing information about the activity of one or more areas of a brain network to provide treatment.

It is another object of the methods and systems of the invention to provide a brain neuromodulation device to one or more sensory pathways based upon the functional or anatomical connectivity of one or more areas of a brain network.

It is another object of the invention to provide a method of treatment wherein target brain regions are selected based upon characteristics of brain networks in which they participate.

It is another object of the invention to provide a method of neuromodulation of several brain areas using a neuromodulation protocol which incorporates the fact that these modulate each other, for example, by compensating for connections between brain structures. It is another object of the invention to provide a method of neuromodulation of multiple areas of a brain network so that the relative activations or other characteristics are controlled in a desired manner.

It is another object of the invention to provide a method of neuromodulation of multiple areas of a brain network by modulating two or more brain target regions included in a brain network underlying the disorder, wherein stimulation in one brain target is modified, at least in part, based upon stimulation in another of the targets.

It is another object of the invention to provide a method of neuromodulation of one or more areas of a brain network underlying the disorder, wherein the activity of at least one brain region is modulated in relation to the activity sensed for at least a second brain region.

It is another object of the invention to provide a method of neuromodulation which includes treating different characteristics of a disorder by adjusting stimulation in different regions of a network.

It is another object of the invention to provide a method of neuromodulation which uses algorithms to link the neuromodulation protocol of one stimulated area to those used at a different modulated area.

It is another object of the invention to provide a method of neuromodulation which comprises alternating between two or more target brain regions of a network to deter the emergence of adaptation and neural compensation as may occur, for example, via endogenous homeostatic mechanisms.

These and other objects will be described and will provide systems and methods of neuromodulation which will greatly improve treatment of various neurological disorders.

The systems and methods will now be described in greater detail, with reference to detailed illustrative embodiments. It will be apparent that systems and methods of the invention may be embodied and modified in a variety of manners without departing from the scope and spirit of the description.

BRIEF DESCRIPTION OF THE DRAWINGS

FIG. 3 is a graphic representation of the stochastic resonance effect.

DETAILED DESCRIPTION

Figure 1:
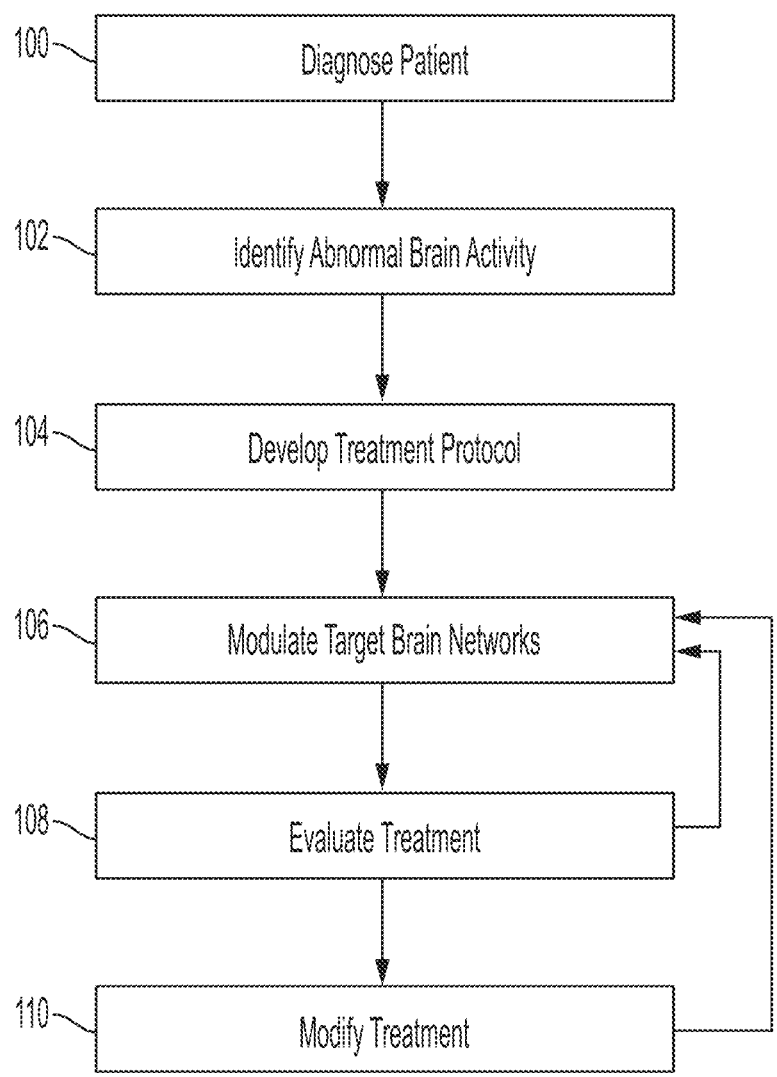
FIG. 1 is a flow chart illustrating the method of the invention.

The following material provides definitions for terms used in this application. However, these terms may be expanded upon and/or modified according to the various specific alternative embodiments which will be described.

As used herein, "brain modulation system" (BMS) refers to a system which provides neuromodulation of brain networks. The BMS may be realized using a "brain neuromodulation device" (BND), for example an apparatus such as an audio stimulator, a visual stimulator, a mechanical stimulator or combined audio and visual stimulator. The BND may be a commercially available generic device which can be adapted to approximately achieve the intended neuromodulation of a brain network as described herein. A BMS can also utilize a BND which is a transcranial electrical stimulator to provide electrical stimulation. A BMS can be realized completely within a BND, but may also exist in a distributed fashion. For example, the BND may communicate with an external patient programmer which can be used to program the BND, and which comprises a part of the BMS. The BMS, and its methods, can include the utilization of sensed data which is sensed by external instrumentation such as an EEG, MEG or fMRI device. BNDs can be partially or completely external, and can be devices which are affixed to anatomical structures.

As used herein, the terms "brain network", "brain pathway", or "brain circuit", refer to two or more brain regions for which at least first brain area has been shown to modulate at least a second brain area. A brain network which that is identified for treatment would normally contain at least one brain area that has been associated with a symptom for which therapy is sought. A symptom can be, for example, an undesirable behavioral, emotional, cognitive, brain or sensory process or state. A brain network can also be comprised of several divisions (i.e., nuclei, or a specialized group of cells), within a particular brain structure, such as the thalamus, since divisions within a structure can modulate activity in other divisions of that structure, either directly, or via a multi-synaptic pathway. A network can be considered pathological when it is associated with a brain disorder. The pathology can be reflected, for instance, by sensed data which is evaluated relative to a threshold, or in relation to normal, expected, or desired activity, as may be defined by treatment criteria.

As used herein, "brain disorder" refers to at least one characteristic or symptom of a psychiatric, mood, neurological, movement, epileptic, behavioral, addiction, attentional, psychological, or other central nervous system disorder. The brain disorder can also be a thought processes disorder, a memory disorder, a "mental disorder", an age-related disorder, a cognitive or other disorder of neural origin. Brain disorders can also include pain disorders, migraine, headache, stroke, and other types of traumatic brain injury. The psychiatric disorders can include, for example, forms of psychosis, anxiety disorders, schizophrenia, and obsessive-compulsive disorder. Rather than being defined by a particular behavior or DSM criteria, a brain disorder may be defined as an abnormality as may be evidenced from analysis of neuroimaging data, such as an abnormal MEG, EEG or QEEG profile. This abnormal activity may be associated with structures of a relevant network using source analysis methods.

As used herein, the term "neuroimaging" can refer to either functional or structure neuroimaging. The term "sensing" includes performing sensing using neuroimaging.

As used herein, the term "functional neuroimaging", refers to any method which provides information about an amount, or changes in amount, of brain a characteristic including blood flow, neurotransmitter level, metabolism, electrophysiological activity, and includes information obtained from either acutely/chronically implanted sensors or external sources. Functional neuroimaging includes implanted electrodes or other sensors which provide estimates of neuro-physiology/neurochemistry/metabolism or other measure correlated with the function of brain regions. Further, functional neuroimaging can include techniques such as electro-encephalography (EEG) obtained from either scalp or implanted electrodes, magneto-encephalography (MEG), evoked-potential (EP), functional magnetic resonance imaging (fMRI), and other magnetic resonance imaging techniques such as magnetic resonance spectroscopy (MRS). Functional neuroimaging includes analysis of neuroimaging data according to conventional techniques known to those skilled in the art. Further, neuroimaging (and collection of self-norms) can occur before, during, and/or after treatment, and can occur when a patient is resting, engaged in a cognitive, emotional and/or other task, and can occur while patients are exposed to medication and/or while drug free. Neuroimaging may occur using one or more tasks to assess different symptoms related to the disorder, for example, one task can pertain to measurement of sadness or anxiety, while another can assess hopelessness.

As used herein "treatment protocol" refers to the protocol used by the treatment program to provide treatment. The treatment protocol has parameters which define the locations for sensing and stimulating operations, and can contain parameter values for the sensing protocol, the stimulation/modulation protocol, and the evaluation protocol. The treatment protocol defines the treatment criteria, the reference values and any other parameter value which is used to provide specific neuromodulation treatment. A treatment protocol can be designed to cause the treatment program to directly modulate regions of the brain network, or the regions to be modulated can be modulated indirectly by stimulation of neural targets in a different area.

As used herein the terms "sensing protocol/parameters" define how sensing is accomplished and can include placement of sensors, measurement of sensed data including when, if, and what data is sensed, and how the sensed data is processed. The sensing protocol determines the sensing parameters, for example, sensing rate, type, and location. Sensing protocols, including processing of sensed data, can be guided by network interaction data. Sensing operations are provided by the sensing subsystem.

As used herein the terms "modulation-protocol/parameters" and "stimulation-protocol/parameters" define how stimulating is accomplished and can include placement of stimulators, stimulation/modulation protocols including when, if, for how long stimulation is presented, and which stimulation signals are used to stimulate one or more brain regions. The "parameters" refer to the settings used while achieving the protocol. The stimulation protocol determines the stimulation parameters, for example, stimulation frequency band, intensity, location and duration. The stimulation protocol can be completely predefined or can also include providing modulation based upon evaluation of sensed data, using data as a control signal. Stimulation operations are provided by the stimulation sub-system.

As used herein the terms "evaluation protocol/parameters" define how sensed data is evaluated. For example, the evaluation protocol defines if the data are compared to reference values such as self-norms, population norms, or selected threshold values. Evaluation of sensed data can be non-statistical, involving simply the utilization of the data to create a stimulation signal using control laws or filters. The evaluation protocol selects treatment criterion according to the treatment protocol, determines how sensed data are compared to reference values using treatment criterion, Evaluation operations are normally provided by the control subsystem. Further, as used herein, the terms "evaluate the sensed data", "evaluate treatment", "data analysis", "analysis protocol", can refer to the methods and protocols used analyze the sensed data. Data analysis can include the step of "processing sensed data" which can refer to signal processing of the sensed data, and processing of the sensed data which converts it into meaningful units. "Using sensed data" can entail simple processing of the data. An, example of using sensed data is feeding it through a circuit to create a stimulation signal, as may occur using control laws. Evaluating the sensed data can comprise several different types of processing including, assessing the sensed data using a criterion which is either met or failed, performing a statistical assessment relative to reference values stored in the database, using measurements of the sensed data in an equation, model, correlation analysis, or algorithm, which provides result data.

As used herein the terms "control protocol/parameters" refers to the subroutine of the treatment protocol that determines what to do if the treatment criterion is met or not met. As used herein "reference values" refer to values such as self-norms or population norms, values determined by an equation, fixed values, percentage values, or ratio values.

As used herein, the terms "modulate" and "stimulate" (and hence "neuromodulation" and "neurostimulation") refer to causing a change in brain activity, chemistry, or metabolism. The change can refer to an increase, decrease, or even a change in a pattern of neuronal activity.

Neurostimulation may be either excitatory or inhibitory stimulation, and may be at least auditory, visual, mechanical, electrical or a combination of two or more of these. When two or more regions are stimulated, one type of stimulation can be excitatory while the other is inhibitory.

While prior art examples provide a number of useful advantages for treatment of various disorders, none provide such therapy using neurostimulation specifically designed for the treatment brain networks. In the treatment of tremor, the therapy can be provided by disrupting activity, such as hyper-synchrony, in regions of the motor cortex. In the treatment of seizures, the therapy can be provided in order to disrupt the emergence of epileptiform activity, and stimulation can occur in an area where this increased synchrony was detected. While treatment of these disorders may also benefit from network stimulation, sufficient relief can obviously occur when stimulation is designed with respect to stimulating a specific site, regardless of the state of the network in which it is a part. In contrast, psychiatric and other higher order disorders of consciousness certainly involve distributed brain networks, and relative activation as well as communication between different nodes of the network underlie various aspects of the disorder, and must be taken into account in order to provide improved treatment outcome.

The existence of brain networks, and methods for identifying the brain regions involved in these networks, is well known. Evidence indicates that activation of one area is functionally significant in relation to the state of the rest of the network within which that activation takes place. The state of the network is likely just as important as the activation itself with respect to the functional role of that network. In other words, the functional relevance of a brain area depends on the status of other connected areas i.e., the context within which the region is operating. As Mcintosh (2004) notes "A region can participate in several behaviors through variations in its interactions with other areas". "Contexts and catalysts: a resolution of the localization and integration of function in the brain." *Neuroinformatics.*

2004; 2(2):175-82. Studies have explored the relationship of neural networks to different brain disorders, including disorders of consciousness or with aging and have demonstrated pathology in the primary networks of different disorders as well as the existence of putative compensatory networks However, while networks underlying both normal and pathological functioning, as well as networks related to different characteristics of various brain disorders, have been well documented, these have not been incorporated into the techniques used to create, or adjust, treatment methods in the emerging field of neuromodulation. The prior art, and current practice, approach stimulation of one or more regions as if these were isolated structures and the operational principle is simply summation: if stimulation of one area is useful, two might even be more so. This strategy fails to utilize the growing understanding provided by studies of neural synchrony and brain networks, which forms the basis of the methods of the current invention.

Evaluating and treating networks using neurostimulation is more promising than treating individual brain targets. Even when neuroimaging procedures indicate normal activity levels in regions of a brain network, the communication between two or more nodes of a network may be abnormal. Accordingly, therapeutic stimulation may strive not only to increase, decrease, normalize, positively/negatively reinforce, or otherwise modulate the relative activity of different regions of a path or network, but can also be designed to alter the interactions which normally exist between these regions. Network interactions may entail modulation of one area by another, which may be positive, negative or both, due to different fiber tracts or "paths" that join the regions of the brain network, and may also include reciprocal interactions. Modulations of one area by another may occur directly or may be mediated by at least one other intervening structure which may receive inputs from other regions of the network as well. In one embodiment, information is utilized about network interactions, and/or neuroanatomical connections, between different regions of the network in order to identify target structures, set the initial neuromodulation protocols, and guide the adjustment of neuromodulation protocols during treatment. Further, using the concepts of transfer entropy, the covariance between stimulus A & stimulus B can be quantitatively decomposed into the effects of stimulus A upon stimulus B, the effect of stimulus B upon stimulus A, and the "mutual information" reflecting the common action of some stimulus C upon both stimulus A & stimulus B By using algorithms which adjust stimulation in one region to that provided in another, based upon, for example, models of networks the brain network can be treated rather than just treating isolated regions without adjusting stimulation in relation to the network or the influence that stimulation at one site may have on another.

Unlike the current invention, the interactions or connectivity between two or more regions of the network, and the effects that stimulation of one target area may have on other target, or on non-target, areas of a network, are also not addressed in the prior art. Incorporating these network dynamics into the treatment methods is a main feature of the current invention. These omissions in the prior art are addressed by novel features of the methods and systems described herein, which thereby offer significant advantages over this art.

FIG. 1 illustrates an example of a method for neuromodulation of brain networks in the treatment of brain disorders. First, a patient is identified 100 as having a brain disorder and also as appropriate for treatment. One or more candidate brain networks which are related to the unwanted symptoms of the disorder are then identified 102 from neuroimaging data. The BND is provided to the patient so that at least one brain network may be stimulated. Modulation of the brain network 106 then occurs in the treatment of the brain disorder. For example, stimulation may occur in two regions in order to compensate for interactions between those regions, and this can occur using linked stimulation rules as will be discussed. In the next step, the effects of the treatment provided by the modulation of the brain network are evaluated 108, and either modulation is then repeated 106 without adjusting the parameters or modulation parameters are adjusted 110, and then modulation 106 again occurs. When neuroimaging data is obtained and treatment is evaluated 108 the data can be compared to reference data using treatment criteria. This comparison may result in either a positive result wherein modulation parameters are adjusted 110, or a negative result wherein modulation parameters are not adjusted, and then stimulation is repeated 106. Alternatively, evaluation of the treatment is not necessary on a regular basis, and neuromodulation treatment simply consists of steps 100 to 106, wherein modulation of at least two areas of a brain network occurs using a stimulation protocol.

With respect to patient identification 100, appropriate patient identification may be based upon a number of criteria selected by the medical experts providing treatment. For example, patients who have been refractory to various medications over a sustained period are obviously prime candidates, as are patients who suffer disorders for which medication is not helpful (e.g., traumatic brain injury). Patients can be selected based upon medical history, psychological or neuropsychological testing, neuroimaging data collected from external sensors, such as the results of structural, and/or functional neuroimaging tests. Patients who demonstrate certain profiles of test results can be compared to profiles of previous patients who either did, or did not, respond well to neuromodulation treatment. In the latter case, the candidate patient may not be selected as appropriate for therapy.

With respect to identification of brain networks 102 which will be modulated during treatment, in one embodiment, sensed regions, target regions and neuromodulation parameters for treatment may be chosen either based upon the knowledge gained from the patient or from population data. The data can include models of the putative brain networks responsible for a particular brain disorder and appropriate targets of the network can be identified prior to treatment. A comparison of a model of the patient's brain networks to models of networks of prior patients for whom treatment was successful can assist in designing the therapy, including selecting treatment sites for sensing and stimulation according to the similarity of a patient's profile with profiles of past patients. For example, in one NBN treatment method a patient can be classified into one of a number of existing sub-groups using discriminant or cluster analysis of measures of the network, or transformed measures (e.g., z-transformed, factor scores, model coefficients). Generally, this method includes the steps of obtaining test results such as neuroimaging data for a patient, making a comparison of the test results of the current patient to past test results of patients who were successfully treated using a particular neuromodulation treatment protocol, classifying the current patient based upon this comparison, selecting a treatment paradigm based upon this classification. Additionally, the one or more targets of a brain network which are chosen for treatment may include structures which have been shown to have functional or structure interaction, for example, due to afferent or efferent pathways which connect the two or more structures, either directly or via at least one intermediary structure, and which are related to the pathological condition. Further, sensed/target regions and neuromodulation protocols may be chosen based upon imaging of a subject's brain, using some of the examples related to identification of brain networks which are provided in the section entitled identification of brain net-works.

In steps 100 through 108, functional imaging data may be used to identify and evaluate the brain networks of a patient before and during treatment. Although the BND can sense data and evaluates this data to guide treatment, the steps of the method of FIG. 1 can occur in a non-automatic fashion under the direction of a physician. During any of the steps of the method, neuroimaging data can be obtained for a subject during one or more conditions including, baseline conditions, (for example, during rest eyes-open, during rest eyes-closed), or during activation while engaged in at least an emotional task, a sensory task, a memory task, a stressor task, cognitive task, target detection task or other type of task which may activate the brain network underlying a characteristic of the brain disorder, or by comparing the resting and activated states. Imaging data may also be obtained for a subject while the subject is presented with stimuli to which a response may, or may not, be required, or using stimuli which have a low or high emotional aspect (e.g., faces with different expressions, unpleasant or disturbing images), or during activation with cues related to a disorder, such as displaying drug paraphernalia to a person with substance abuse disorder or phobic objects to one with a phobia. Subjects may also be asked to internally generate stimuli (e.g., think of an unpleasant experience). Imaging data may also be collected while the patient is exposed to a treatment medication, a substance which may acutely modify or worsen the brain disorder, or a substance which will alter brain activity or metabolism in a useful manner with respect to gaining information about the brain network underlying a characteristic of the disorder. Imaging data across conditions can be manipulated (e.g., subtracting a baseline condition from a task condition), processed, and analyzed using numerous techniques described in the literature. The results can then be used to obtain information related to the brain networks, can be used to assist in determining the placement of the sensors and stimulators, and can be used to adjust both initial as well as subsequent parameters for neuromodulation.

Generally, by measuring the amount of abnormal activity, functional imaging data can be used to quantify the disease state and changes in this state that occur during the treatment of the disorder. Using data about one or more brain networks of the patient and some aspect of the patient's disorder, the relationship between these can be established by imaging techniques such as path/PLS analysis and SEM or transfer entropy computations. Targets for neurostimulation, and candidate neuro-stimulation parameters, can be determined due to aspects of the model analyzed using methods such as correlation of hyper-(or hypo-) activation with some aspect of the disorder, absolute or relative activation, connectivity (path) coefficients, directionality of influences within a network, latency differences between activation of different regions, etc. Alternatively, locations for neurostimulation and the initial stimulation parameters can be determined by any other criteria, such as neuropsychological tests, or other means.

With respect to modulation of brain networks 106, during the treatment of the disorder, the BMS must be programmed and the effects of neurostimulation assessed. BMS neuromodulation treatment protocols can be adjusted by patients or doctors, using an external patient programmer, to modulate the brain network in order to achieve and optimize therapeutic efficacy.

In one embodiment, neurostimulation parameters can be set by the medical personnel based upon the results of functional imaging. The neuromodulation parameters can be adjusted until the target regions are modulated in a desired manner. For example, activity in regions of the network is increased, decreased, or otherwise altered. The results of the functional imaging can be analyzed using path analysis or other analysis which provide a model of the neural network being modulated, and the neuromodulation protocol can be iteratively adjusted until, for example, the model indicates normalization, in other words, that a characteristic of the brain network more closely approximates that found in normal control subject or is otherwise maintained within a specified range.

Neuromodulation treatment can occur continuously, periodically, in response to patient demand, or responsively due to evaluation of sensed data. Additionally, a first protocol can be used for continuous or periodic neuromodulation, while a second protocol which is used in response to patient demand, or in response to evaluation of sensed data, is interspersed with or is used in combination with the first protocol.

With respect to evaluating treatment of the brain networks 108, evaluation can occur by comparing sensed data to reference data, which can be normative data, with respect to treatment criteria. Treatment failure may occur when brain activity of certain regions in the patient's brain deviate from the normative goals embodied by the treatment criteria, and treatment success may be judged by the return of the deviant features to within the normative range. Such change can be quantified by representing the patient's brain state as a multivariate vector (Brain State Vector, or BSV), in a multi-dimensional signal space and using the length of the BSV to quantify the distance from the normative region centered around the origin of the signal space. The BSV can be a vector computed as the difference between normative vector and an abnormal vector, or alternatively the BSV can be computed from z-scores and thus can be both statistically-based and normalized. Effective treatments should shorten the BSV, incorrect treatment may lengthen the BSV, and "side effects" may cause a change or rotation in the direction of the BSV in the signal space. The BSV can be computed upon the components of network model (e.g. SEM) wherein selected components best reflect the state of the disorder being treated. In other words, abnormal activity of the network is normalized or changed to bring an undesirable characteristic of the network closer to a desired level.

In one embodiment, if the desired changes are not reflected in either the subjective experience of the patient, or the data sensed by the implanted sensors, then the neural target area can be changed or an additional neuromodulation target may be chosen. However, it should be noted that alterations of neural firing patterns and adjustments in neurotransmitter and receptor systems which may play important roles in the therapeutic effects of brain stimulation, may have slow time courses, evolving over days or weeks, and accordingly evaluation may not be possible during a single session. In other words, stimulation may not immediately manifest therapeutic benefit.

Sensed data can relate, for example, to at least dopamine, serotonin, GABA or other neurotransmitter level, chemical or electrical activity of a neural population or group of cells, a neurotransmitter metabolite level, a medication or drug level, a hormone level, a blood-borne substance level. Sensed data can also relate to the relative levels of one or more measurements made, either within, across, or between brain regions, or can relate to a change in these levels over time.

Generally, the method of FIG. 1 solves a problem of prior art which teaches neuromodulation for treatment of various brain disorders as if these each are due to a single area of abnormal activity, which is not part of a network. The methods of FIG. 1 are primarily designed with a consideration of the indirect changes which connections between the nodes of the network produce due to stimulation of these nodes. The NBN methods also address the fact that disorders are usually not constrained to a single unwanted characteristic. Multiple unwanted features often characterize a single brain disorder, sometimes simultaneously, but also not, and also to varying degrees. Accordingly, stimulation of a network should differentially treat characteristics of a disorder by specifically modulating areas of the brain that primarily different characteristic of a disorder. In the case of depression, the different characteristics may be sadness, hopelessness, anxiety, antipathy, frustration, indifference, helplessness, or lethargy. Although there is obviously not a one-to-one mapping of these features of the disorder with brain structures, the idea is that stimulation to treat one area should compensate for the effects of this modulation on other areas so that other features are not unintentionally augmented. Characteristics of other disorders for which treatment is sought may be, for example, obsession, compulsion, inattentiveness, hyperactivity, and memory deficits whether recent, short term or episodic. Generally, methods for treating patients with a brain disorder comprise neuromodulation of at least two regions of a brain network, one of which has been at least partially associated with an unwanted characteristic of a brain disorder. While a particular region is being stimulated, the other brain regions are modulated in relation to the stimulation of this region. In this way, the successful treatment of one characteristic of a disorder will not cause changes in a different characteristic, as a side effect of treatment.

Figure 2:
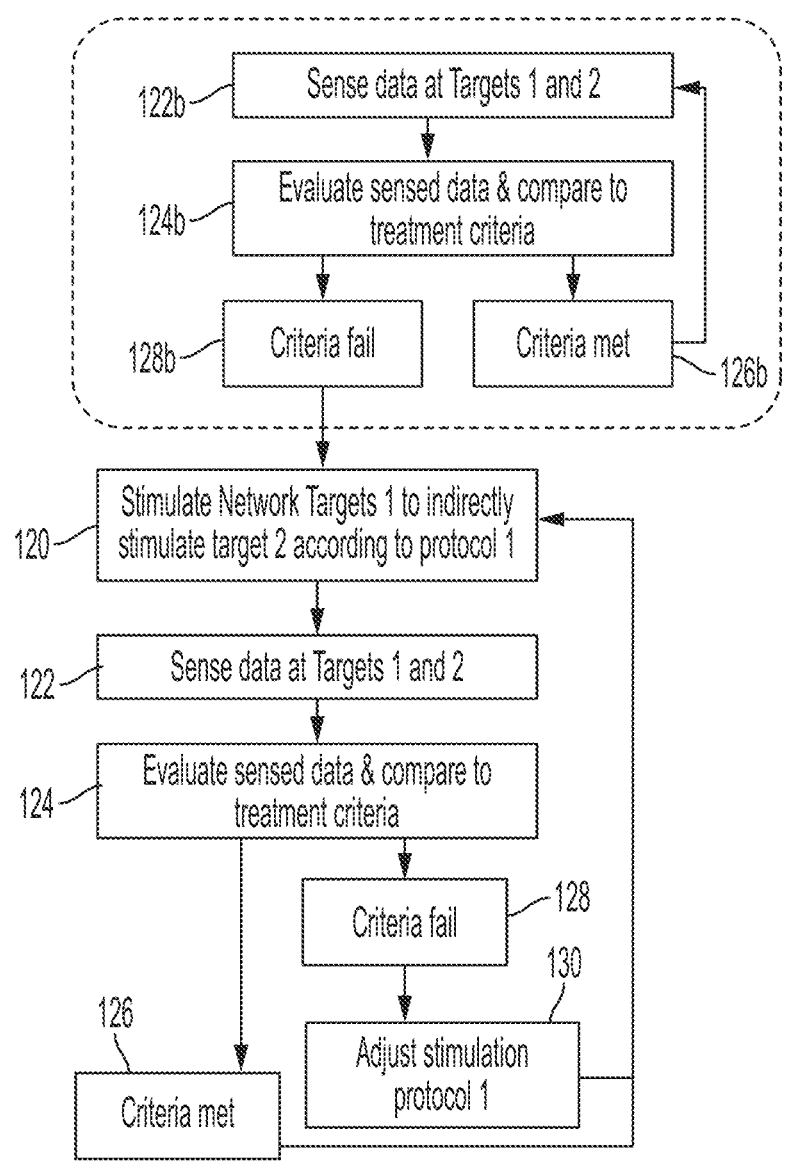
FIG. 2 is a flow chart illustrating an alternative method of the invention where there are two or more targeted brain regions for treatment.
Figure 3A:
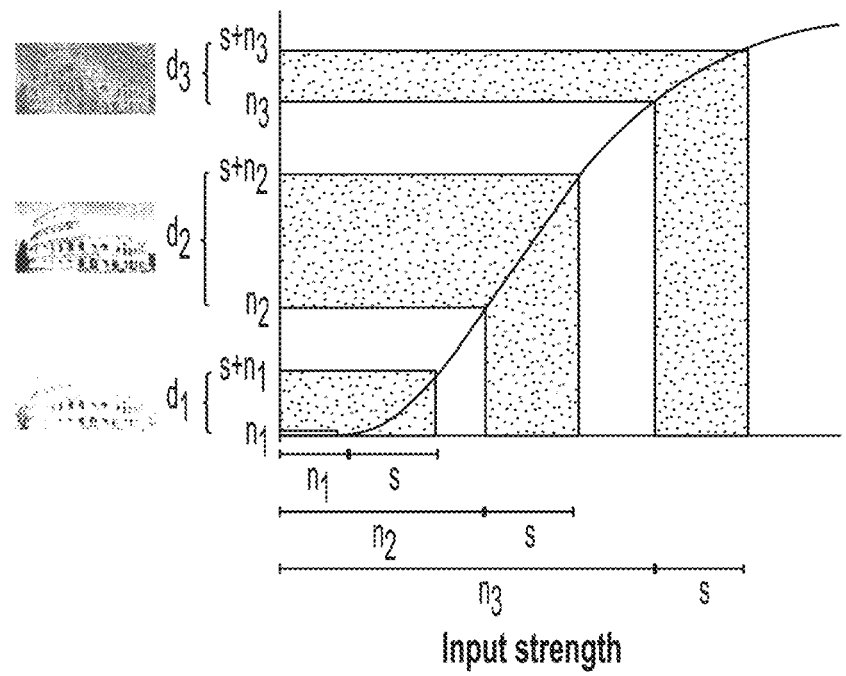
FIG. 3(A) illustrates a sigmoid input-response function. A fixed signal, s, is added to differing levels of noise, n. The differential response, d, to s varies as a function of the size of n: when n is low (n1) or high (n3), d is smaller than when n is at an intermediate level (n2). The function shown here is based on a cumulative gamma function.
Figure 3B:
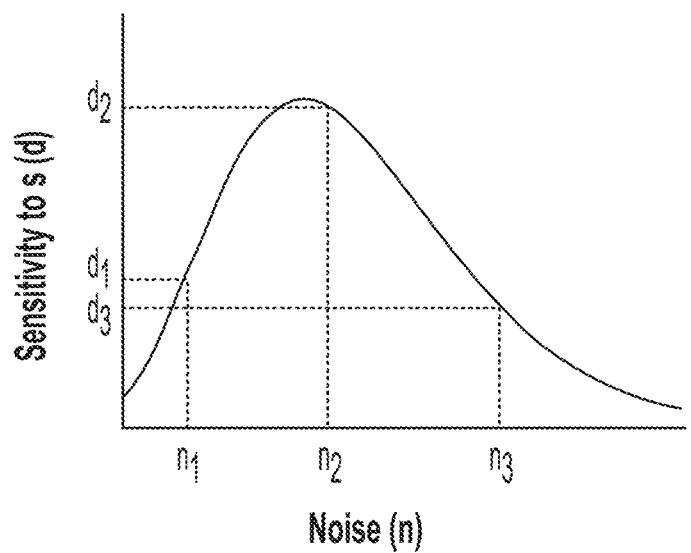
FIG. 3(B) illustrates the sigmoidal function of the stochastic resonance effect. The first derivative of the function in panel A, corresponding to the slope of that function. It shows how, d, the sensitivity of the response to s, changes across all values of n.

In another embodiment, a method of neuromodulation of a brain network for the treatment of a brain disorder includes providing stimulation to a target brain region of the brain network according to a stimulation protocol that produces neuromodulation of the target area as well as modulation of a second brain area of a network, the second area being sufficiently distal from said stimulation that it is not directly modulated by said stimulation 120, (of FIG. 2B). The method may only be step 120, or may also comprise sensing data and adjusting the neurostimulation protocol. These additional steps can include sensing data from at least regions 1 and 2 122, evaluating the sensed data using treatment criteria 124, adjusting said stimulation protocol if one or more of the treatment criteria fail to be met 130, such as the measure of activity in the first and second brain regions being within a specified range, and then repeating stimulation. The treatment in FIG. 2B (lower), is for a continuous stimulation protocol. Of course, this protocol can be made responsive by including the subroutine within the dashed lines, which contains steps 122b-128b, wherein stimulation is not initiated until evaluation of sensed data indicates 124b this is necessary 128b. It is obvious that this routine, or a similar routine can be easily appended to the other methods described herein and shown in other figures.

The identification of numerous brain networks which putatively underlie (i.e., correlate with symptoms of) various brain disorders has come from many areas of neuroscience. Anatomical studies utilizing animal or post-mortem brains, or structural imaging, including computerized tomography (CT), magnetic resonance imaging (MRI), and its variants such as diffusion tensor imaging (DTI), have provided direct and indirect evidence of the role of brain networks, and the individual brain regions of these networks, in normal functioning as well as in various brain disorders. Functional imaging techniques which are accomplished with external sensor or techniques with use acutely or chronically implanted electrodes or neurochemical sensors, and pharmaceutical manipulations have all provided valuable data related to the metabolism, activity, connectivity, and neurochemistry of these brain networks. The targets of the network to be used for neuromodulation treatment can be identified from the results of these previous studies, functional neuroimaging of the patient's brain, or a combination of the two. Prior studies which can be used for identifying brain networks related to pathological affect, can include studies where healthy volunteers were asked to experience an emotion (e.g., sadness, anxiety).

For example, in the case of schizophrenia, and other complex psychiatric disorders, across the population the disorder may engulf a cluster of heterogeneously distributed symptoms, traits, states, and symptoms. Further, within a single patient, several different networks may be primarily responsible for different characteristics of the disorder. For example, using fMRI studies have found that a brain circuit, involving the right amygdale and the MPFC had functional abnormalities during processing of emotion, suggesting a viable brain network for which treatment of dysfunctional emotional behavior in schizophrenia may be applied. Tackling a different aspect of this disorder, an fMRI study related to visually guided saccades and antisaccades, reported involvement by cortical and subcortical networks supporting a model in which the fronto-parietal circuit is related to the planning of saccadic eye movements that involve attention and control, while the fronto-striato-thalamo-cortical circuits connect to cortical region as a feed-back network. Accordingly, since abnormalities in spatial attention and eye movement control observed in schizophrenia may therefore stem from dysfunctions in the fronto-parietal and fronto-striato-thalamo-cortical circuits, these brain networks are appropriate targets for treating within this patient population. Clearly different brain networks underlie the complex characteristics of psychiatric disorders and therefore neuromodulation may attempt to differentially normalize, or otherwise modulate, each of these in order to treat a separate aspect of the disorder. Treatment should be guided not only by considering activation, but also relative activation, compensatory mechanisms, and the nor-mal/abnormal connectivity and interactions within the brain networks that underlie various characteristics of these disorders.

In one embodiment of a treatment protocol which addresses compensating for abnormal connectivity, the activity of one region of a network is used to guide the neurostimulation of at least a second region of the network. Rather than just increasing the activity of a second region of a network, the aim is to correlate the activation of this second region so that its activity is more (or less) correlated with activity in the first region, since neuroimaging data (such as network modeling, in normals, or population norms for imaging data e.g., QEEG normative profiles), indicates that the two regions are normally more coherent. Accordingly, correlation analysis of data from brain networks can be used guide neurostimulation protocols, where the aim is not to increase or decrease the overall level of activity, but rather to alter the timing and correlation, of activity between the two regions of the brain network.

Pre-treatment imaging data may be used to determine network and stimulation parameters in order to provide for more accurate treatment. By evaluating the brain network of the individual, a direct measure of the pathology can be used to create an appropriate treatment protocol, For example, in one method, measures from a brain network of an individual can be statistically compared to different clusters in a database, in order to classify the network of an individual into a particular subclass. One type of classification can be related to treatment successes, wherein different subclasses of networks which have been shown to normalize when stimulation follows a particular treatment protocol created. Classification of the patient, guides the selection of the treatment protocol for that individual. Accordingly, evaluating neural network data can be used to select the numbers, location, and types of stimulus that may be successful in normalizing the network, and consequently increasing the chance for providing successful therapy for the behavioral and cognitive symptoms of a disorder. In one method the steps for treating a brain disorder comprise; sensing neuroimaging data, evaluating neuroimaging data to provide at least one measurement of a brain network, performing a comparison of this measurement of a brain network to a database of two or more classes of brain networks and, using the results of this comparison to assist in selecting a treatment protocol.

Following initial treatment of a patient, the parameters of the neurostimulation protocol can be iteratively determined by performing an assessment process, which examines changes which occur in the brain networks associated with the disorder. During the assessment process the creation of the neurostimulation protocol can be made based upon sensed data obtained from implanted sensors that measure the network's activity with respect to various aspects of electrical activation, biochemical or drug levels, neuronal firing, metabolism, and other measures for which sensors have been implanted. Alternatively, this determination can be used based upon sensed data which is neuroimaging data obtained from external sensors. Activation of different regions of the network, as well as other characteristics of the network can be obtained by modeling the imaging data and can be used to guide the neuromodulation protocol. The neuroimaging data can be sensed data that is collected during neuromodulation using a treatment protocol which stimulates the target regions, or only a portion of the neural targets, within at least one network which putatively underlies a characteristic of the disorder. This data can be used to determine the effects which stimulating portions of the network have on other portions. The treatment protocol can incorporate information about the inter-region interactions which change stimulation of a target region based upon the stimulation at least one other target region.

In another embodiment, the sensed data can be used to modify stimulation protocols, whereby the sensed data is processed to provide result data, and result data can be evaluated to adjust the neuromodulation protocol. The sensed data can, for example, be amplified and filtered, and the power within a specified band is measured to yield result data. The result data is evaluated, for example, compared to a treatment criterion, which may be based upon reference data. The success or failure of the result data to meet the treatment criterion will determine if stimulation parameters are maintained or adjusted, respectively. In another example, the result data are processed by mathematical models which evaluate the brain network, such as path models. This modeling produces result data which can be compared to treatment criteria in order to determine if treatment should be initiated, or, if already occurring, determine if it should continue with or without adjustment.

This specification has described a number of embodiments of methods and systems for modulating brain networks in the treatment of brain disorders. Although the text of this specification often discusses treatment of at least one network, it should be understood that neuromodulation systems can be bilateral, and for a network in each hemisphere may be modulated based upon sensed data or characteristics of the ipsilateral network.

Alternatively, neuromodulation of a brain networks can be based upon sensed data, from the contralateral network, or may be based upon data sensed from structures in networks on both sides of the brain. Additionally, neuromodulation of a brain networks in one hemisphere can treat one characteristic of the disorder, while neuromodulation of brain networks in the other hemisphere can treat a different characteristic of the disorder.

Patents, patent publications, and other documents referenced in this specification are hereby incorporated by reference for the substance of what they contain.

I claim:

1. A brain neuromodulation device, comprising:
at least one stimulator configured to output a sensory stimulus to a sensory organ of a user of the brain neuromodulation device in accordance with stimulation parameters, wherein the sensory stimulus is a bandwidth-limited stochastic stimulus configured to stimulate sensory neurons within the sensory organ, the sensory organ forming part of a sensory pathway, the sensory pathway being connected to one or more brain regions in one or more brain networks of the user, thereby modulating neural activity within a brainwave frequency band or bands in the one or more brain regions in the one or more brain networks, wherein the sensory organ is selected from the group consisting of an auditory sensory organ, a visual sensory organ, a vestibular sensory organ, and a tactile sensory organ;
at least one storage device configured to store a neuromodulation protocol; and
controller circuitry configured to:
transmit the stimulation parameters to the at least one stimulator in accordance with the neuromodulation protocol; and
receive input data indicating an effect of the modulation of neural activity in the one or more brain regions in the one or more brain networks in response to stimulating the sensory neurons in the sensory organ of the user with the bandwidth-limited stochastic stimulus; and
adjust the stimulation parameters transmitted to the at least one stimulator based, at least in part, on the received input data.

2. The brain neuromodulation device of claim 1, further comprising at least one sensor configured to acquire the input data used to adjust the stimulation parameters.

3. The brain neuromodulation device of claim 1, wherein the controller circuitry is further configured to receive the input data from at least one sensor external to the brain neuromodulation device.

4. The brain neuromodulation device of claim 1, wherein the controller circuitry is further configured to receive the input data from one or more electroencephalography (EEG) sensors.

5. The brain neuromodulation device of claim 1, further comprising a communication interface, wherein the communication interface is configured to receive the neuromodulation protocol from an external computer connected to the communication interface.

6. The brain neuromodulation device of claim 1, wherein adjusting the stimulation parameters based, at least in part, on the input data comprises comparing the input data to reference data indicating a normative state of the one or more brain networks.

7. The brain neuromodulation device of claim 1, wherein the neuromodulation protocol is selected based, at least in part, on a brain disorder associated with the user, wherein the brain disorder is selected from the group consisting of a thought process disorder, a memory disorder, a mental disorder, an age-related disorder, and a cognitive disorder.

8. The brain neuromodulation device of claim 1, wherein the bandwidth-limited stochastic stimulus is configured to inhibit and/or desynchronize neural oscillations in at least one of the brain regions in the one or more brain networks.

9. The brain neuromodulation device of claim 1, wherein the at least one stimulator includes a first stimulator configured to output a first sensory stimulus and a second stimulator configured to output a second sensory stimulus.

10. The brain neuromodulation device of claim 9, wherein the first sensory stimulus is configured to stimulate sensory neurons in a first sensory organ of the user and the second sensory stimulus is configured to stimulate sensory neurons in a second sensory organ of the user different from the first sensory organ.

11. The brain neuromodulation device of claim 9, wherein the first sensory stimulus is a first bandwidth-limited stochastic stimulus to modulate neural activity within a first brainwave frequency band and the second sensory stimulus is a second bandwidth-limited stochastic stimulus to modulate neural activity within a second brainwave frequency band different from the first brainwave frequency band.

12. The brain neuromodulation device of claim 1, wherein the stimulation parameters include timing parameters for the sensory stimulus.

13. The wearable neuromodulation device of claim 12, wherein the timing parameters indicate whether the sensory stimulus is to be presented continuously, intermittently, or in response to the occurrence of a condition.

14. A method of providing neuromodulation using a brain neuromodulation device, the method comprising:
    storing a neuromodulation protocol in at least one storage device of the brain neuromodulation device;
    transmitting stimulation parameters to at least one stimulator in accordance with the neuromodulation protocol;
    outputting, by the at least one stimulator, a sensory stimulus to a sensory organ of a user of the brain neuromodulation device in accordance with the stimulation parameters, wherein the sensory stimulus is a bandwidth-limited stochastic stimulus configured to stimulate sensory neurons within the sensory organ, the sensory organ forming part of a sensory pathway, the sensory pathway being connected to one or more brain regions in one or more brain networks of the user, thereby modulating neural activity within a brainwave frequency band or bands in the one or more brain regions in the one or more brain networks, wherein the sensory organ is selected from the group consisting of an auditory sensory organ, a visual sensor organ, a vestibular sensory organ, and a tactile sensory organ;
    receiving input data indicating an effect of the neuromodulation modulation of neural activity in the one or more brain regions in the one or brain networks in response to stimulating the sensory neurons in the sensory organ with the bandwidth-limited stochastic stimulus; and
    adjusting the stimulation parameters transmitted to the at least one stimulator based, at least in part, on the input data.

15. The method of claim 14, wherein adjusting the stimulation parameters based, at least in part, on the input data comprises comparing the input data to reference data indicating a normative state of the one or more brain networks.

16. The method of claim 14, wherein outputting a sensory stimulus comprises outputting a first bandwidth-limited stochastic stimulus to modulate neural activity within a first brainwave frequency band and outputting a second bandwidth-limited stochastic stimulus to modulate neural activity within a second brainwave frequency band different from the first brainwave frequency band.

17. A brain neuromodulation device, comprising:
    at least one stimulator configured to output a sensory stimulus to a sensory organ of a user of the brain neuromodulation device in accordance with stimulation parameters, wherein the sensory stimulus is a bandwidth-limited stochastic stimulus configured to stimulate sensory neurons within the sensory organ, the sensory organ forming part of a sensory pathway, the sensory pathway being connected to one or more brain regions in one or more brain networks of the user, thereby modulating neural activity within a brainwave frequency band or bands in the one or more brain regions in the one or more brain networks, wherein the sensory organ is selected from the group consisting of an auditory sensory organ, a visual sensory organ, a vestibular sensory organ, and a tactile sensory organ;
    at least one sensor configured to sense an effect of the modulation of neural activity in the one or more brain regions in the one or more brain networks as a result of stimulating the sensory neurons in the sensory organ with the bandwidth-limited stochastic stimulus; and
    controller circuitry configured to:
        transmit the stimulation parameters to the at least one stimulator in accordance with a first neuromodulation protocol;
        receive feedback from the at least one sensor to determine the effect of modulation of neural activity in the one or more brain regions in the one or more brain networks; and
        adjust the stimulation parameters transmitted to the at least one stimulator based, at least in part, on the received feedback.

* * * * *

UNITED STATES PATENT AND TRADEMARK OFFICE
CERTIFICATE OF CORRECTION

PATENT NO. : 10,625,042 B2
APPLICATION NO. : 15/034328
DATED : April 21, 2020
INVENTOR(S) : Steven Metzger Page 1 of 1

It is certified that error appears in the above-identified patent and that said Letters Patent is hereby corrected as shown below:

In the Claims

In Claim 14, at Column 18, Line 7-8:
"….effect of the neuromodulation modulation of neural activity…."

Should read:
….effect of the modulation of neural activity….

Signed and Sealed this
Twenty-first Day of July, 2020

Andrei Iancu
*Director of the United States Patent and Trademark Office*